US00PP20812P3

(12) United States Plant Patent
Scully et al.

(10) Patent No.: US PP20,812 P3
(45) Date of Patent: Mar. 9, 2010

(54) CENTIPEDEGRASS PLANT NAMED 'BA-417'

(50) Latin Name: *Eremochloa ophiuroides*
Varietal Denomination: BA-417

(76) Inventors: Brian Thomas Scully, 110 Conaskonk Cir., Royal Palm Beach, FL (US) 33411; Robert Lee Beiriger, 16356 Trafalgar Dr. E., Loxahatchee, FL (US) 33470; Kevin E. Kenworthy, 5164 SW. 82nd Terrance, Gainesville, FL (US) 32608; Joseph Bryan Unruh, 4895 Pineview Ridge, Pace, FL (US) 32571; Russell Toshio Nagata, 25 Nalani St., Hilo, HI (US) 96720

( * ) Notice: Subject to any disclaimer, the term of this patent is extended or adjusted under 35 U.S.C. 154(b) by 0 days.

(21) Appl. No.: 12/006,777

(22) Filed: Jan. 7, 2008

(65) Prior Publication Data

US 2009/0178169 P1 Jul. 9, 2009

(51) Int. Cl.
*A01H 5/00* (2006.01)

(52) U.S. Cl. ..... Plt./388

(58) Field of Classification Search ..... Plt./388
See application file for complete search history.

(56) References Cited

OTHER PUBLICATIONS http://www.environmentalturf.com/images/ourgrasses/media/Hammock.pdf (web-archived Oct. 7, 2006) (1 pages total).*
http://www.turfgrasstrends.com/turfgrasstrends/article/articleDetail.jsp?id=193850&pageID=2 (3 pages total).*
http://www.gcsaa.org/newsweekly/2005/feb/4/product.asp (5 pages total).*

* cited by examiner

*Primary Examiner*—Susan B McCormick Ewoldt

(57) ABSTRACT

A newly discovered, and asexually prorogated genotype of Centipedegrass with a distinct set of agronomic, horticultural, and morphological traits.

7 Drawing Sheets

Latin name of the genus and species: *Eremochloa ophiuroides* (Munro) Hack

GENUS AND SPECIES NAME

This invention relates to a new and distinct genotype of Centipedegrass of the genus and species *Eremochloa ophiuroides* (Munro) Hack. It is described herein and designated as 'BA-417'. As used herein, 'BA-417' has the identical meaning as "Hammock Centipede".

BACKGROUND OF THE INVENTION

This invention was discovered and identified in central Palm Beach County, Fla. It was one of a number of unique and distinctly different vegetative off types/inclusions growing adjacent to an uncultivated area that was initially used for driveways and a parking area. With time, a portion of this area was eventually paved and crudely landscaped with a common unknown population of centipedegrass. The centipedegrass was planted and maintained as a fringe around the paved driveways, the grassed parking lots, and used as the transition vegetation in the understory of the pine and palmetto wooded area around the church yard and its parking areas. Because this area of sandy woodland soil was only intended to be sporadically maintained with very low inputs, centipedegrass was chosen for this turf application. As a species, centipede grass typically requires minimal cultivation, survives dryland conditions, and exhibits weed suppression through allelopathy.

'BA-417' was originally propagated asexually from a single 6.0 inch stolon taken from the off type inclusion noted above in the summer of 1997. 'BA-417' was chosen from a group of advanced lines initially selected as off types in an undeveloped and unimproved population of centipedegrass, which is consistently known and recognized throughout the turf industry and in the scientific literature as "Common" centipedegrass. Over a four year research period 'BA-417' was vegetatively propagated multiple times and evaluated at three research sites in Florida. Throughout multiple vegetative increases, 'BA-417' has remained uniform and genetically consistent. The denomination of this new invention is 'BA-417', but in commerce 'BA-417' will be marketed under the synonym "Hammock Centipede", which is its commercial designation in the United States.

The distinctness of 'BA-417' from 'Centennial' (unpatented) and its progenitor, the "Common" population of centipedegrass, is based on four sets of traits including: 1) floral morphology; 2) leaf and stem morphology; 3) color and pigmentation; and 4) rate of growth and cover.

For the purpose of registration under the "International Convention for the Protection of New Varieties of Plants" (generally known by its French acronym UPOV Convention) and noting Sections 1612 of the Manual of Patent Examination Procedures this new variety of Centipedegrass of the present invention is named 'BA-417'.

DETAILED DESCRIPTION OF THE VARIETY

Figure 1:
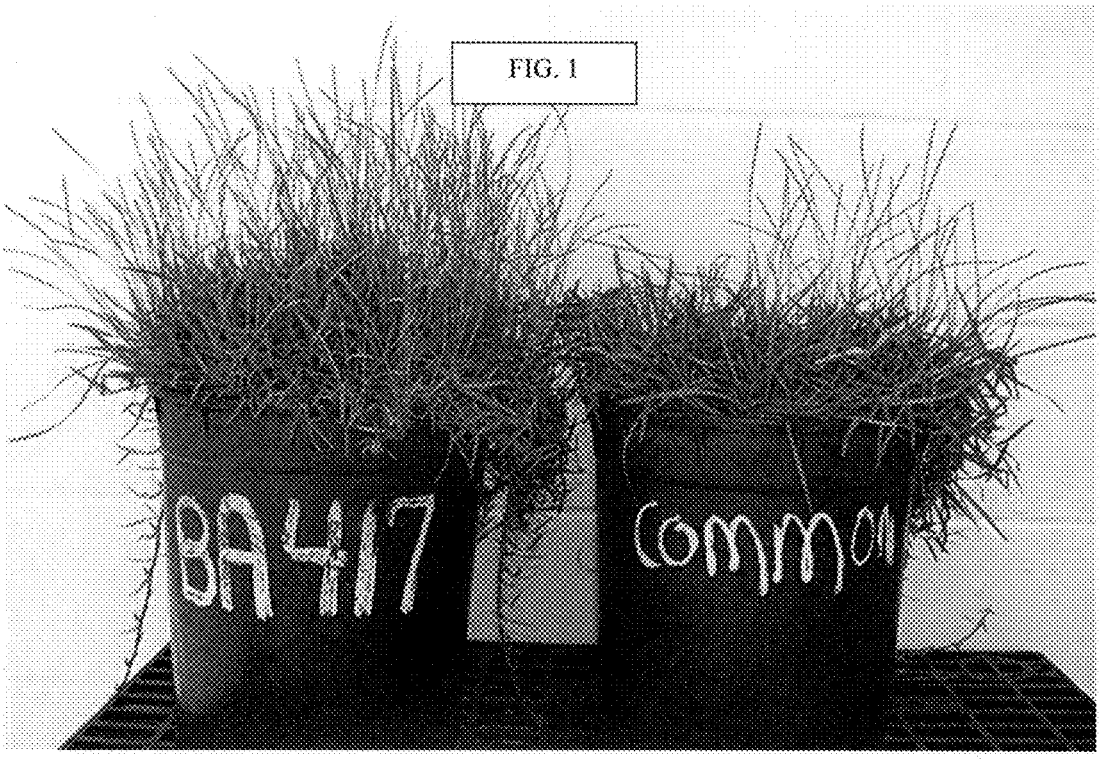
FIG. 1: A comparative photograph of 'BA-417' and the "Common" population of centipedegrass. These pots were grown side-by-side, uncut and under identical cultural practices. This photograph illustrates morphological differences among the varieties.
Figure 2:
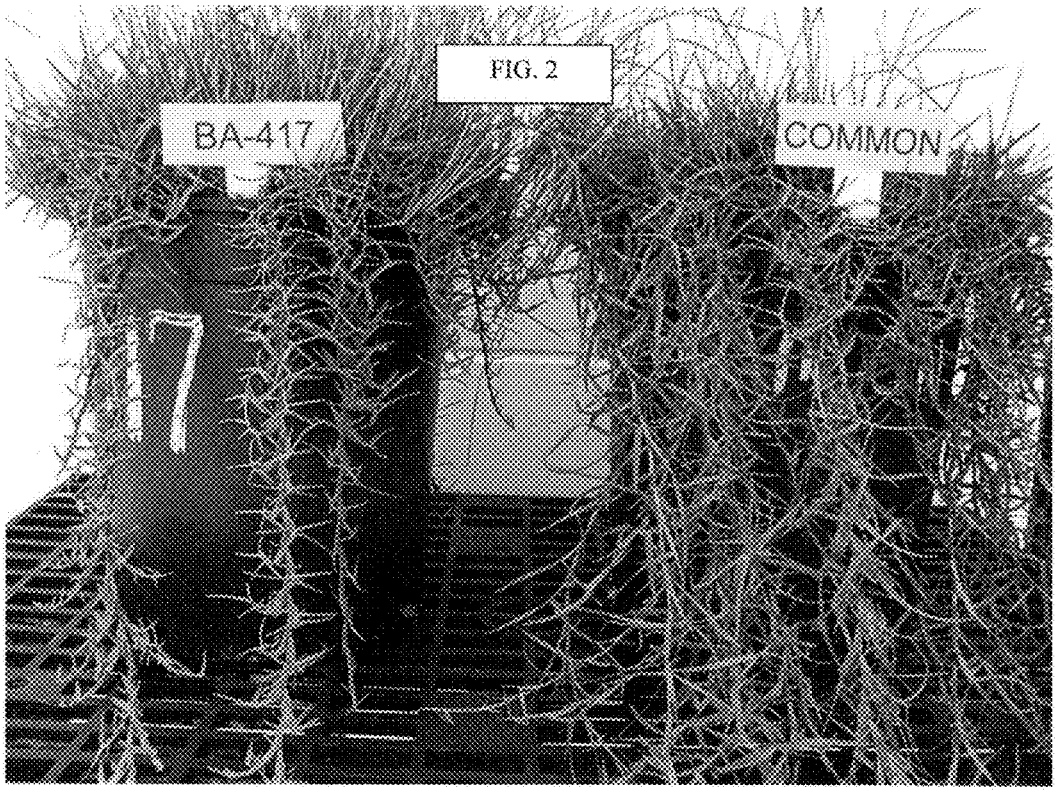
FIG. 2: A comparative photograph of 'BA-417' and the "Common" population of centipedegrass illustrating morphological differences in stolons. These pots were grown side-by-side, uncut and under identical cultural practices.
Figure 7:
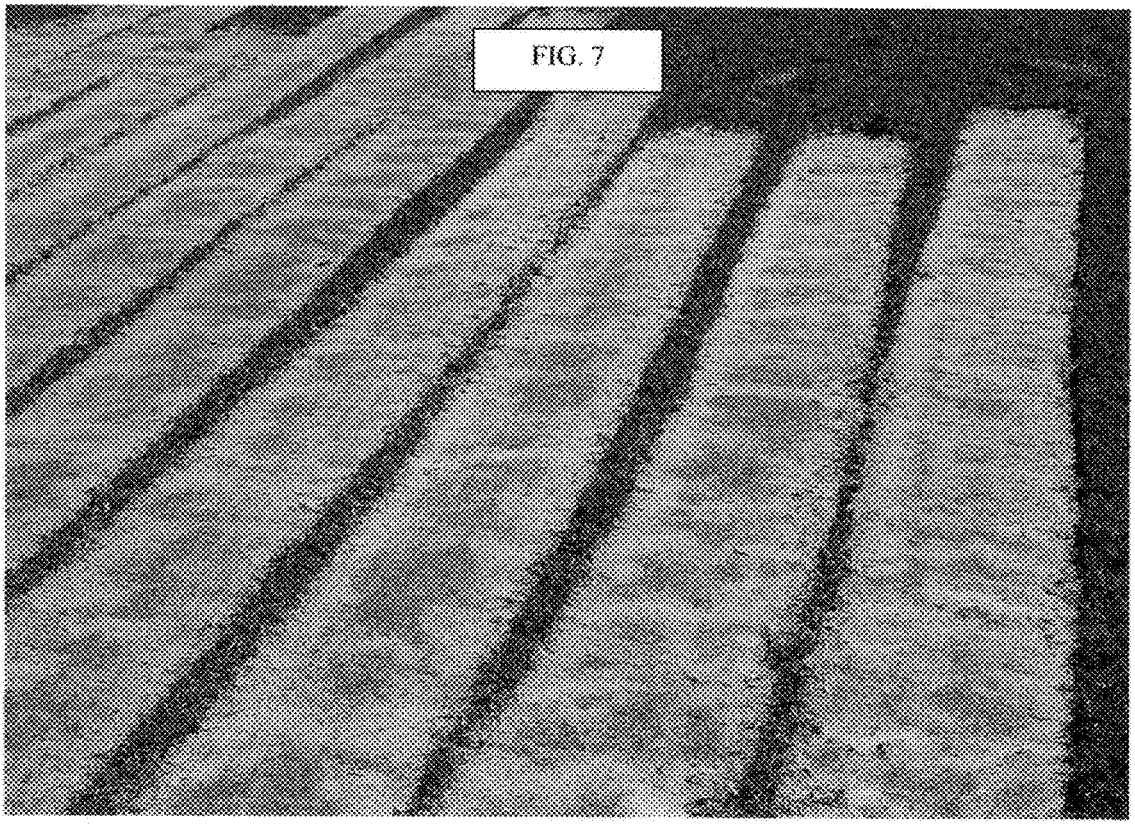
FIG. 7: A aerial photograph of 'BA-417' after a recent cutting.

This new variety of Centipedegrass is a perennial warm season turf species that is stoloniferous, branched and prostrate against the ground surface (FIG. 2 and FIG. 7), with leaves, roots and reproductive structures that can arise from the same node and ultimately forms a dense sward and subsequent thatch structure. This new variety of plant is propagated asexually from either stolons, sprigs, or plugs (FIG. 2). It is best adapted to the subtropical climates of Florida. 'BA-147' was tested and described under field conditions at three research sites in Florida, including Arcadia, Belle Glade, and Milton. 'BA-417' was phenotypically compared to 'Centennial', an unpatented variety developed by Auburn University (Pedersen and Dickens, 1985), and the undeveloped and unimproved population of centipedegrass typically referred to as "Common" centipedegrass. 'BA-417' displayed a closer morphological likenss to 'Centennial' (unpatented) than to the "Common" centipedegrass for floral, leaf and stolon traits. But, 'BA-417' was distinct from these standards for vegetative color, pigment, and the rate of "grow-in".

Floral morphology was described by five measured traits, and 'BA-417' differed from the standard varieties for four of the five traits. Overall, 'BA-417' produced an average inflorescence that was significantly longer than either 'Centennial' (unpatented) or "Common" centipedegrass (Table 1). The average peduncle and seed head length was also longer on 'BA-417' than the two standard varieties. Proportionately, the seedhead accounted for 38.6% of the overall inflorescence length on 'BA-417'. 'Centennial' (unpatented) and "Common" centipedegrass had 40.3% and 45.9% of the inflorescence length as seedhead tissue. The average number of seeds per seedhead ranged from 19.15 to 20.70. On a density basis, 'Centennial' (unpatented) had the most compact arrangement with 4.19 seeds/cm of raceme length, while 'BA-417' and "Common" centipedegrass had seeds less densely arranged on the raceme with 3.68 and 3.78 seeds/cm of raceme length, respectively. A unique feature of these centipede grasses was the propensity to produce rudimentary or secondary spikelets on the seedhead. 'BA-417' produced significantly fewer secondary spiklets than either 'Centennial' (unpatented) or "Common" centipedegrass (Table 1).

The morphology of the flag leaf was described by three traits, which included the flag leaf length and width, along with the sheath length. 'BA-417' differed from "Common" centipedegrass for the dimensions of all three flag leaf traits. For each flag leaf trait 'BA-417' had a more robust morphology (Table 2). The flag leaves of 'BA-417' averaged 68.6% longer and 52.5% wider than "Common" centipedegrass. The flag leaf sheaths of these varieties were keeled, with pubescent margins that overlapped from the base. For 'BA-417' the length of the flag leaf sheaths were 18.3% longer than the sheaths on "Common" centipedegrass. This more robust morphology of the flag leaf traits was consistent with the larger floral morphology of 'BA-417'.

The morphology of the vegetative tissue was measured by the dimensions of leaf length and width, and the internode length and width. For all three test varieties, the leaves were similarly erect, linear, rigid, and shiny, with variable apices. There were no unique or noteworthy taxonomic differences in the structure or characteristics of the leaf collar, ligules or sheaths among the tested varieties. The morphology of the internode tissue of 'BA-417' was intermediate in dimensions when compared to 'Centennial' (unpatented) and "Common" centipedegrass, while the vegetative leaf tissue was smaller than standard varieties (Table 3). The internodes are mostly smooth, solid and somewhat oval with leaves that emerged basally from moderately hairy nodes that are highly branched. The leaf length of 'BA-417' was shorter than 'Centennial' (unpatented) and "Common" centipedegrass, but only the difference between 'BA-417' and "Common" centipedegrass was statistically relevant (Table 3). 'BA-417' produced leaves that were nearly 10.0 mm or 28% shorter than "Common" centipedegrass. Compared to the standard varieties, 'BA-417' had narrower leaves as well. The differences in leaf width were not significant among the varieties, and only had a 0.15 mm range. The internode length of 'BA-417' was not significantly different from either standard variety, but all three varieties differed statistically for internode width (Table 3). In general, the smaller leaf structures of 'BA-417',-along with intermediate internode traits conferred a finer texture to the appearance of 'BA-417'.

An integrated measure of canopy appearance, texture and color is assessed by the overall quality rating (Table 4). In each summer month, 'BA-417' had a significantly higher rating than "Common" centipedegrass. Similarly, 'BA-417' produced superior quality ratings as compared to 'Centennial' (unpatented), but these values were not statistically significant (Table 4).

The color and pigment deposition in 'BA-417', "Common" centipedegrass and 'Centennial' (unpatented) varied when fresh samples of vegetative tissue were compared to color panels in the Munsell Color Chart (1977). The adaxial leaf surface of 'BA-417' ranged in hue from 2.5GY TO 7.5GY and exhibited more variation than either "Common" centipedegrass or 'Centennial' (unpatented) (Table 5). 'BA-417' also had lighter values and less color saturation then either "Common" centipedegrass or 'Centennial' (unpatented). In contrast, the green internode tissue on the stolons of 'BA-417' had a consistently greener hue of 7.5GY compared to 'Centennial' (unpatented) (Table 5). The ranges of the internode color values were different for each variety, but overlapped somewhat. 'BA-417' and 'Centennial' (unpatented) had more color saturation (4-6) than "Common" centipedegrass, which ranged from (6-8). Anthocyanin deposition in the internode tissue produced the expected red (5R) and redish purple (5RP) hues in each variety (Table 5). 'BA-417' consistently had a deeper red and reddish purple pigmentation than either "Common" centipedegrass or 'Centennial' (unpatented), and 'BA-417' had a color saturation value intermediate to the other varieties. The node color for each variety was also different, with some overlap in the range of color parameters (Table 5). These categorical differences in color contributed to the integrated measure of canopy appearance presented above.

These grasses had significantly different patterns of growth and rates of "grow-in" (Table 6). Over the duration of the growth experiment 'BA-417' differed significantly from 'Centennial' (unpatented) in four of the twelve months, while "Common" centipedegrass differed in five of the twelve months. These differences had a seasonal pattern. 'BA-417' and 'Centennial' (unpatented) had significantly slower growth rates during the winter months, while "Common" centipedegrass continued to grow more aggressively through the colder weather. This pattern continued through the spring, but these differences were only significant in May (Table 6). For all three varieties, the most rapid increase in growth occurred in the spring months of March and April, but this was expected. In the early spring, 'BA-417' exhibited an increase in plot cover of 43.3% between March and April, while 'Centennial' (unpatented) and "Common" centipedegrass had increases in coverage of 33.3% and 38.3%, respectively. From an initial 1% cover, all three varieties attained 50% coverage between the sixth and seventh month after planting. 'BA-417' had accelerated growth in the spring and summer months; 'BA-417' had significantly more plot coverage than 'Centennial' (unpatented) from March onward, and significantly more coverage than "Common" centipedegrass from July onward (Table 6). The average stolon number and average stolon length could only be visually distinguished through the first six months of these experiments, but 'BA-417' differed statistically from "Common" centipedegrass for stolon number in three of these six months, and from 'Centennial' (unpatented) in the month of January (Table 6) (FIG. 2). For the average stolon length, 'BA-417' only differed from "Common" centipedegrass in two of the six months. Although these differences were statistically significant, it was difficult to discern a consistent pattern or trend in the growth of stolon numbers and stolen length among the three varieties.

Figure 3:
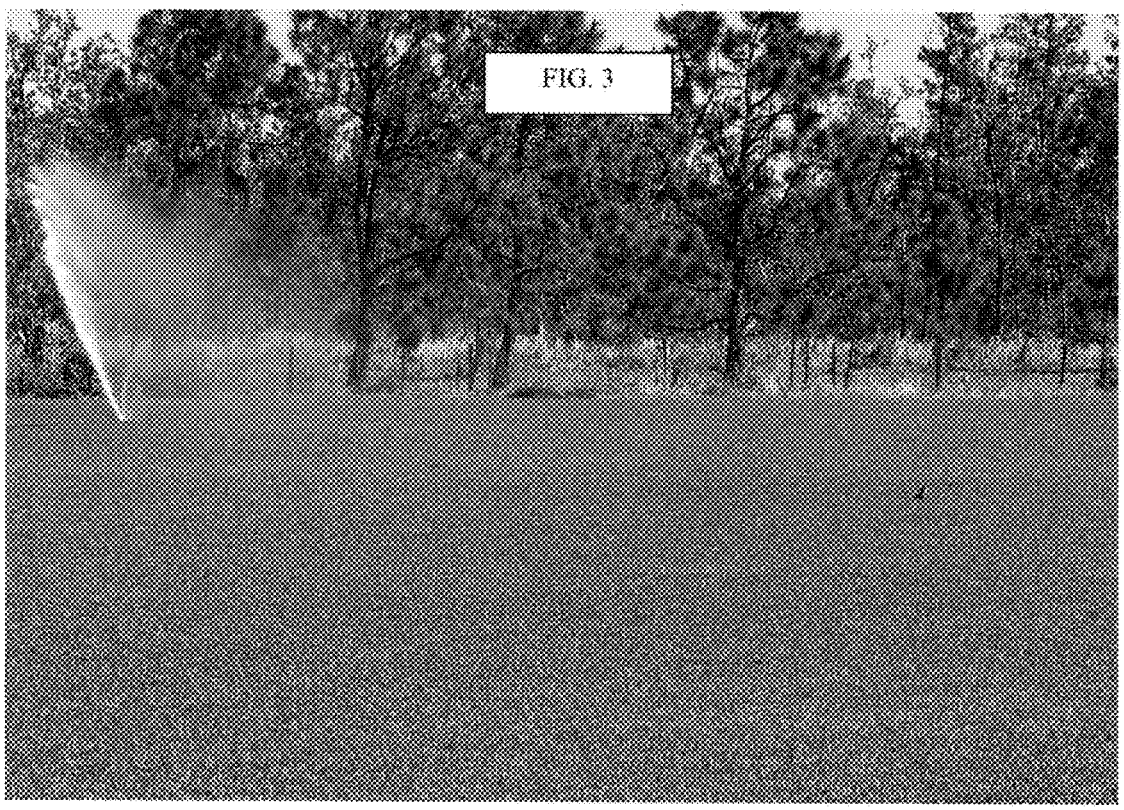
FIG. 3: A Breeders Block of 'BA-417' growing in Avon Park, Fla.
Figure 4:
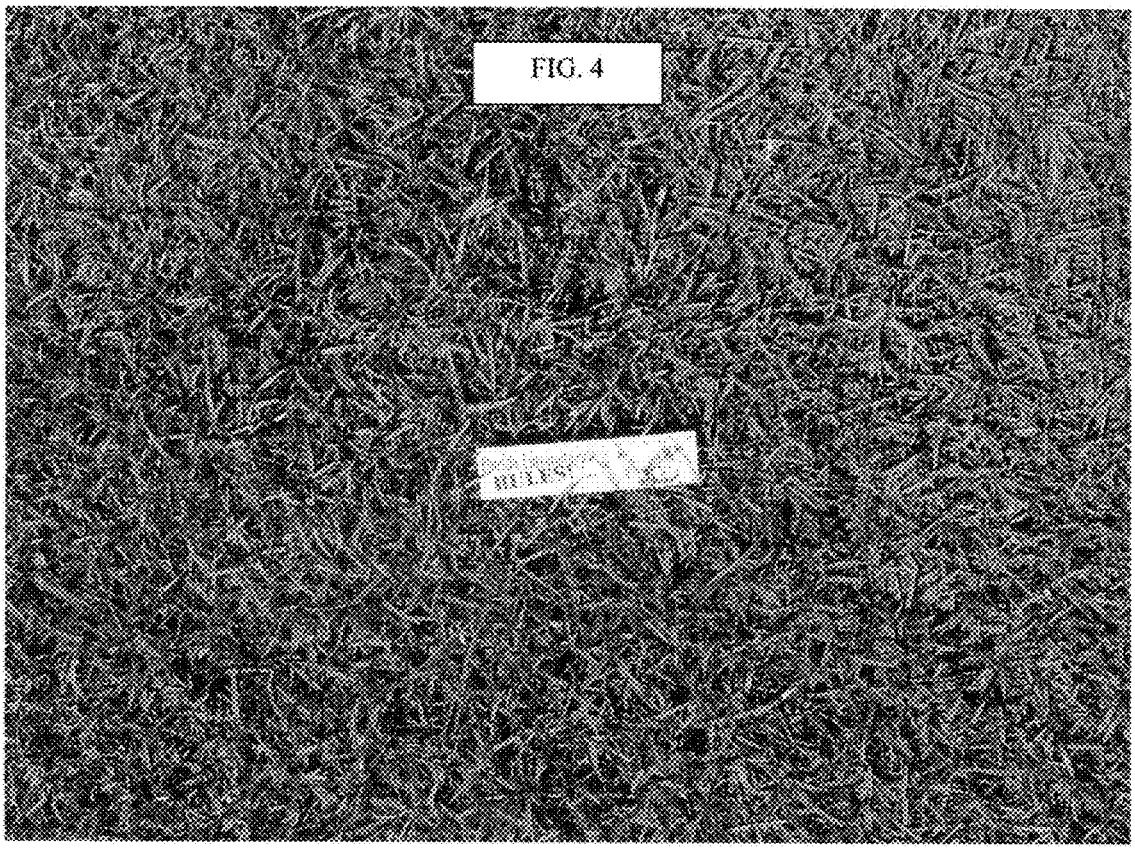
FIG. 4: A close-up photograph of the Breeders Block of 'BA-417' showing leaf morphology.
Figure 5:
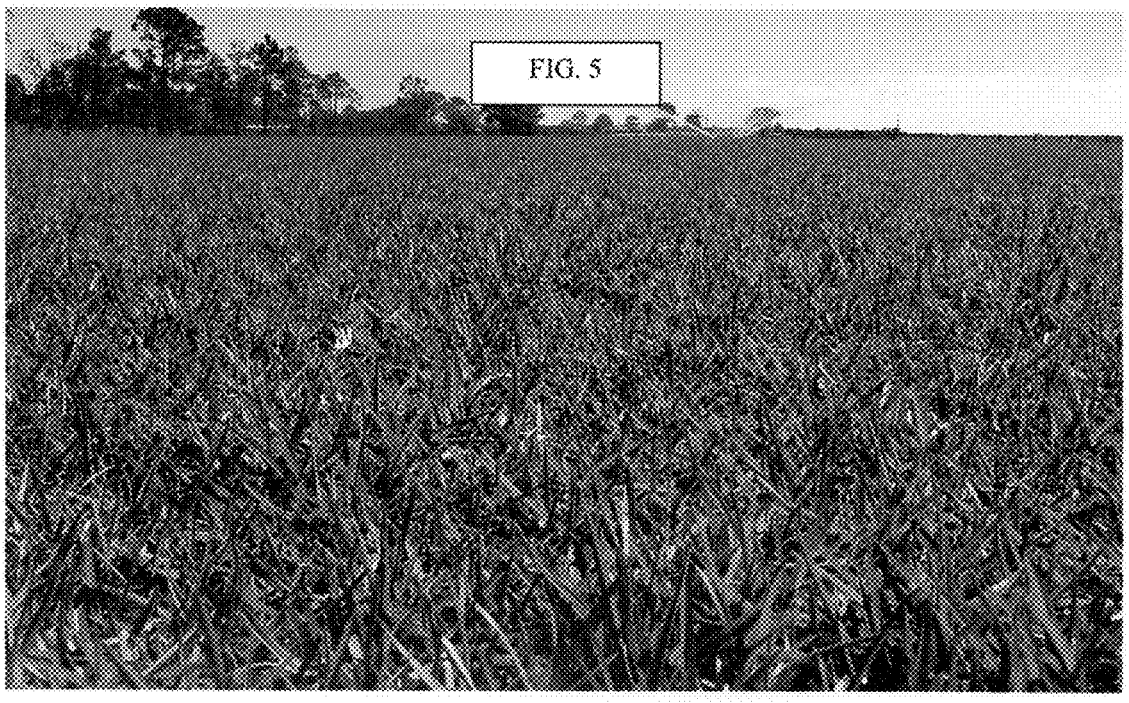
FIG. 5: A close-up photograph of 'BA-417' showing the leaf canopy.
Figure 6:
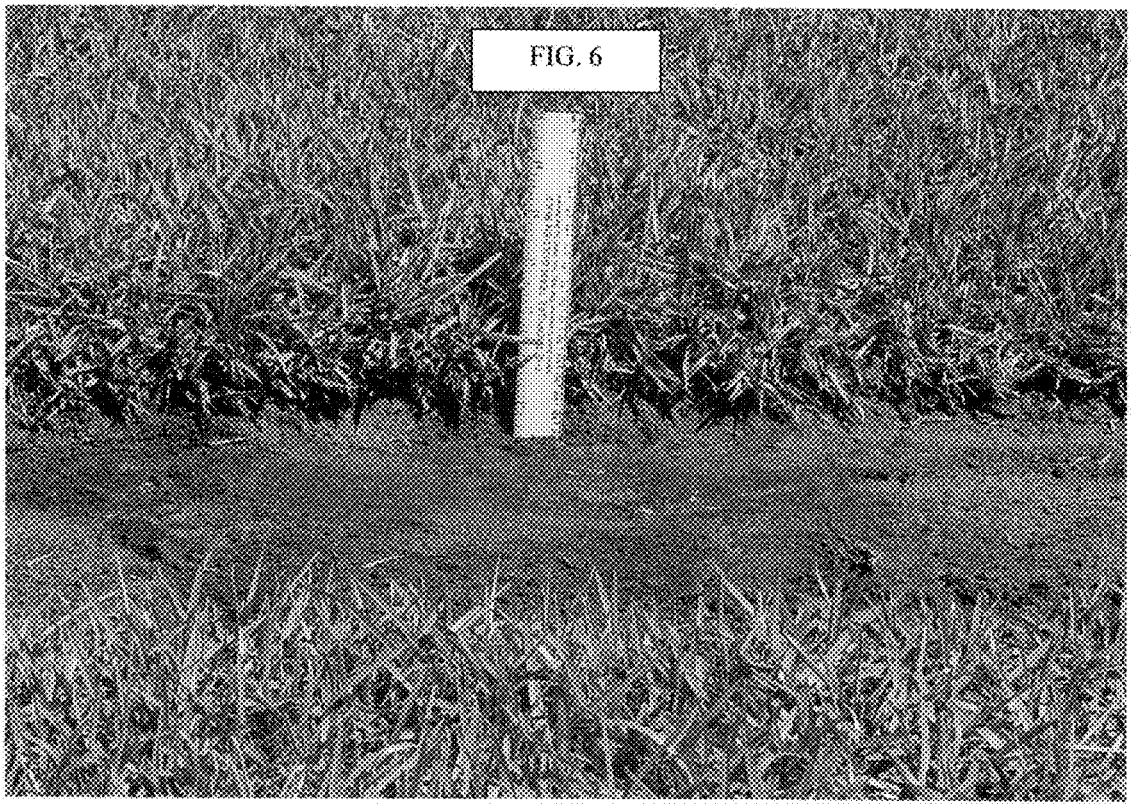
FIG. 6: A side profile photograph of 'BA-417' after a recent cutting.

The results of the first "grow-in" study were repeated with similar results in a second "grow-in" study in Milton, Fla. (Table 7A). In this case, the plots were planted in January with an initial coverage of 5%, and progressed through the summer. 'BA-417' had statistically more coverage than either "Common" centipedegrass and 'Centennial' (unpatented) in the months of March, April, May, and June. By July, 'BA-417' had grown in completely, and 'Centennial' (unpatented) nearly so (Table 7A). "Common" centipedegrass lagged behind and was statistically different from 'BA-417' and 'Centennial' (unpatented). All three genotypes had filled the plots by late August (Table 7A). 'BA-417' completely covered the plots in six months, while "Common" centipedegrass and Centennial took seven months. 'BA-417' reached 50% coverage by the second month of the experiment; while "Common" centipedegrass required five months and 'Centennial' (unpatented) required four to five months to attain 50% plot coverage. A Breeders Block (FIG. 3) of 'BA-417' was also planted in January, but in Avon Park, Fla. It attained 100% coverage in six months (Table 7B).

TABLE 1

Comparison of floral traits among 'BA-417', 'Centennial' (unpatented), and "Common" centipedegrass.

| Trait | 'BA-417' | | 'Centennial' (unpatented) | | "Common" centipedegrass | | LSD |
|---|---|---|---|---|---|---|---|
| (in cm) | Mean | ± s.e. | Mean | ± s.e. | Mean | ± s.e. | $\alpha \leqq 0.05$ |
| Overall Shoot Length[z] | 14.36 | 0.67 | 12.27 | 0.36 | 11.03 | 0.41 | 1.419 |
| Seed Head Length[y] | 5.54 | 0.10 | 4.94 | 0.10 | 5.06 | 0.09 | 0.273 |
| Peduncle Length[x] | 8.82 | 0.61 | 7.33 | 0.32 | 5.98 | 0.40 | 1.293 |

TABLE 1-continued

Comparison of floral traits among 'BA-417', 'Centennial' (unpatented), and "Common" centipedegrass.

| Trait | 'BA-417' | | 'Centennial' (unpatented) | | "Common" centipedegrass | | LSD |
|---|---|---|---|---|---|---|---|
| (in cm) | Mean | ± s.e. | Mean | ± s.e. | Mean | ± s.e. | $\alpha \leqq 0.05$ |
| Seed Count/ Seed Head[w] | 20.40 | 0.58 | 20.70 | 0.49 | 19.15 | 0.46 | 1.450 (ns) |
| Spiklets/Seed Stalk[v] | 1.10 | 0.07 | 1.90 | 0.14 | 1.50 | 0.11 | 0.321 |

[z]Overall shoot length is a measure of the total inflorescence length from the apex of the seed head to the first node on the peduncle subtending the raceme, and measured in cm.

[y]Seed Head Length is measured from the apex of the seed head to the top of the peduncle at the base of the raceme.

[x]Peduncle Length is the average peduncle length measured from the base of the seed head to the top of the node.

[w]Seed Count/Seed Head is the average number of seeds per head or raceme.

[v]Spiklets/Seed Stalk is an average of the count.

TABLE 2

Comparison of flag leaf traits between 'BA-417', and "Common" centipedegrass Centipedegrass.

| Trait (in cm) | 'BA-417' Mean | 'BA-417' ± s.e. | "Common" centipedegrass Mean | "Common" centipedegrass ± s.e. | LSD $\alpha \leqq 0.05$ |
|---|---|---|---|---|---|
| Flag Leaf Length | 28.02 | 1.11 | 16.62 | 1.88 | 4.43 |
| Flag Leaf Width[z] | 3.02 | 0.02 | 1.98 | 0.12 | 0.28 |
| Sheath Length[y] | 46.18 | 1.46 | 39.03 | 1.24 | 3.87 |

[z]Flag Leaf Width is measured at the widest part of the leaf.

[y]Sheath Length is measured from the apex of the base of the flag leaf to the first node subtending the inflorescence.

TABLE 3

Comparison of leaf traits among 'BA-417', 'Centennial' (unpatented), and "Common" centipedegrass.

| Trait (in cm) | 'BA-417' Mean | 'BA-417' ± s.e. | 'Centennial' (unpatented) Mean | 'Centennial' (unpatented) ± s.e. | "Common" centipedegrass Mean | "Common" centipedegrass ± s.e. | LSD $\alpha \leqq 0.05$ |
|---|---|---|---|---|---|---|---|
| Leaf Length | 33.61 | 1.84 | 39.04 | 1.72 | 43.22 | 2.75 | 6.10 |
| Leaf Width[z] | 3.20 | 6.08 | 3.26 | 0.14 | 3.35 | 0.12 | 0.31 |
| Internode Length | 20.27 | 1.03 | 20.86 | 1.12 | 17.91 | 0.59 | 2.67 |
| Internode Width[y] | 2.03 | 0.04 | 1.68 | 0.06 | 2.34 | 0.10 | 0.20 |

[z]Leaf Width is measured at the widest point.

[y]Internode Width is measured at the widest point.

TABLE 4

Comparison of ratings for "Summer-Quality" among 'BA-417', "Common" centipedegrass, and 'Centennial' (unpatented)[Z].

| Variety | MONTH JUNE | JULY | AUGUST | SEPTEMBER |
|---|---|---|---|---|
| "Common" centipedegrass | 7.00 b | 7.00 c | 6.75 c | 6.75 cd |
| 'Centennial' (unpatented) | 7.75 a | 7.75 bc | 7.75 abc | 8.00 ab |
| 'BA-417' | 8.00 a | 8.50 ab | 8.25 ab | 8.25 a |
| LSD $\alpha \cong 0.05$ | 0.68 | 1.13 | 1.28 | 1.14 |

[Z]Summer Quality is an integrated assessment of texture, color, and overall appearance measured on a 1.0 to 9.0 scale (9.0 = Best), during the growing season.

TABLE 5

Color and pigmentation comparison of vegetative tissue of "Common" centipedegrass, 'BA-417', and 'Centennial' (unpatented) based on the Munsell Color Chart.

| | Vegetative Tissue "Common" centipedegrass | 'BA-417' | 'Centennial' (unpatented) |
|---|---|---|---|
| Leaf Color[Z] | 5GY(4/6-8) to 7.5GY(5/4) | 2.5GY(5-6/2) to 7.5GY(5-6/4) | 5GY(4-5/4-6) to 7.5GY(4-5/2-4) |
| Stolon Color[Y] | | | |
| Green Tissue | 2.5GY(5-6/6-8) to 5GY(4-5/6-8) | 7.5GY(5-7/4-6) | 5GY(4-6/4-6) |
| Pigment Tissue | 5RP(3-4/6-8) | 5RP(3/6) to 5R(3/6) | 5GY(4-6/4-6) to 5R(3-4/2-4) |
| Node Color | 5RP(3/2) to 5R (3/2) | 5RP(3-4/4) to 2.5R(4/4) | 5RP(3-4/2) to 5RP(3-4/2) |

[Z]Leaf Color was measured on the adaxial leaf surface.
[Y]Stolon Color was assayed on green internode tissue including the green portion and the portion of the internode suffused with anthocyanins,
[X]Node Color was measured on the node at the junction point between the internodes.

TABLE 6

Comparison of average cover, stolon number and stolon length among 'BA-417', "Common" centipedegrass and 'Centennial' (unpatented) measured on a monthly basis.

| Trait/Variety | SEPTEMBER | 1 OCTOBER | 2 NOVEMBER | 3 DECEMBER | 4 JANUARY | 5 FEBRUARY | MONTH MARCH | 7 APRIL |
|---|---|---|---|---|---|---|---|---|
| Cover[Z] | | | | | | | | |
| 'BA-417' | 1.0 | 3.33 ± 0.33 | 5.33 ± 0.33 | 11.67 ± 6.67 | 14.00 ± 2.08 | 20.00 ± 2.89 | 28.33 ± 4.41 | 71.67 ± 10.93 |
| 'Centennial2 | 1.0 | 3.33 ± 0.33 | 4.33 ± 0.33 | 13.33 ± 1.67 | 13.33 ± 1.67 | 19.00 ± 3.79 | 26.67 ± 7.26 | 60.00 ± 14.43 |
| "Common" | 1.0 | 2.67 ± 0.33 | 6.67 ± 1.67 | 13.33 ± 3.33 | 19.00 ± 2.08 | 33.33 ± 3.33 | 41.67 ± 6.01 | 80.00 ± 5.00 |
| Stolon Number[Y] | | | | | | | | |
| 'BA-417' | 0 | 5.00 ± .058 | 6.00 ± 1.53 | 5.67 ± 1.20 | 7.33 ± 0.33 | 11.33 ± 1.76 | 10.33 ± 2.03 | — |
| 'Centennial' | 0 | 4.67 ± 0.33 | 4.67 ± 0.67 | 4.67 ± 0.67 | 11.67 ± 1.45 | 10.33 ± 2.40 | 11.00 ± 1.00 | — |
| "Common" | 0 | 3.00 ± 1.08 | 4.67 ± 0.88 | 4.33 ± 0.33 | 9.00 ± 2.08 | 15.33 ± 1.76 | 15.67 ± 2.33 | — |
| Stolon Length[X] | | | | | | | | |
| 'BA-417' | 0 | 4.00 ± 0.58 | 6.67 ± 2.19 | 6.67 ± 1.45 | 11.33 ± 1.76 | 4.75 ± 0.85 | 14.67 ± 2.67 | — |
| 'Centennial' | 0 | 4.33 ± 0.88 | 4.67 ± 1.20 | 6.00 ± 1.15 | 11.33 ± 1.33 | 3.50 ± 1.19 | 13.67 ± 1.86 | — |
| "Common" | 0 | 2.33 ± 0.67 | 7.67 ± 1.20 | 6.00 ± 1.15 | 17.33 ± 0.67 | 5.33 ± 0.30 | 18.67 ± 2.91 | — |

| Trait/Variety | 8 MAY | 9 JUNE | 10 JULY | 11 AUGUST | 12 SEPTEMBER | 13 OCTOBER |
|---|---|---|---|---|---|---|
| Cover[Z] | | | | | | |
| 'BA-417' | 73.33 ± 3.33 | 91.67 ± 1.67 | 97.00 ± 0.0 | 99.00 ± 1.00 | 99.00 ± 1.00 | 100.00 ± 0.00 |
| 'Centennial' | 70.00 ± 2.89 | 83.33 ± 4.41 | 86.67 ± 6.01 | 94.00 ± 2.08 | 94.00 ± 2.08 | 98.33 ± 1.45 |
| "Common" | 85.00 ± 5.00 | 93.33 ± 1.67 | 95.67 ± 0.67 | 98.00 ± 1.00 | 96.67 ± 1.67 | 98.03 ± 1.00 |
| Stolon Number[Y] | | | | | | |
| 'BA-417' | — | — | — | — | — | — |
| 'Centennial' | — | — | — | — | — | — |
| "Common" | — | — | — | — | — | — |
| Stolon Length[X] | | | | | | |
| 'BA-417' | — | — | — | — | — | — |
| 'Centennial' | — | — | — | — | — | — |
| "Common" | — | — | — | — | — | — |

[Z]Cover is measured as the cumulative percentage of cover over a prescribed plot area.
[Y]Stolon Number is a count of stolons/rhizomes radiating from a central plug over a prescribed plot area.
[X]Stolon Length is a measure of the average length in cm of the stolons/rhizomes.

TABLE 7A

Comparison of average cover among 'BA-417', "Common" centipedegrass, and 'Centennial' (unpatented) grown at the research site in Milton, FL.

| | Cumulative Coverage Increase (%) | | | |
|---|---|---|---|---|
| Variety | JANUARY | FEBRUARY | MARCH | APRIL |
| "Common" centipedegrass | 5.00 a | — | 25.00 b | 27.50 d |
| 'Centennial' (unpatented) | 5.00 a | — | 22.50 b | 40.00 cd |
| 'BA-417' | 5.00 a | — | 75.00 a | 77.50 a |
| LSD $\alpha \leqq 0.05$ | — | — | 20.80 | 18.90 |

| | Cumulative Coverage Increase (%) | | | |
|---|---|---|---|---|
| Variety | MAY | JUNE | JULY | AUGUST |
| "Common" centipedegrass | 40.00 c | 50.00 d | 67.50 d | 100.00 a |
| 'Centennial' (unpatented) | 60.00 b | 75.00 b | 97.50 a | 100.00 a |
| 'BA-417' | 95.00 a | 92.50 a | 100.00 a | 100.00 a |
| LSD $\alpha \leqq 0.05$ | 15.50 | 13.00 | 15.00 | — |

[z] Cover is measured as the cumulative percentage cover over a prescribed plot area.

TABLE 7B

Rate of coverage increase of the Breeders Block of 'BA-417' grown in Avon Park, FL and pictured in FIG 2.

| | Cumulative Coverage Increase (%) | | | |
|---|---|---|---|---|
| Variety | JANUARY | FEBRUARY | MARCH | APRIL |
| 'BA-417' | 1.00 | 2.00 | 12.00 | 25.00 |

| | Cumulative Coverage Increase (%) | | | |
|---|---|---|---|---|
| Variety | MAY | JUNE | JULY | AUGUST |
| 'BA-417' | 45.00 | 80.00 | 100.00 | 100.00 |

[z] Cover is measured as the cumulative percentage cover over a prescribed plot area.

The invention claimed is:

1. A new and distinct genotype of Centipedegrass plant with a more refined leaf structure as demonstrated by significantly shorter and narrower leaves than the standard vegetatively propagated varieties of centipedegrass.

* * * * *